US 6,728,341 B1

(12) United States Patent
Puchek et al.

(10) Patent No.: US 6,728,341 B1
(45) Date of Patent: Apr. 27, 2004

(54) MONITORING AND COMMUNICATION SYSTEM FOR STATIONARY AND MOBILE PERSONS

(75) Inventors: Daniel R. Puchek, San Antonio, TX (US); Nicholas J. Webb, Wrightwood, CA (US)

(73) Assignee: Royal Thoughts, LLC, Minneapolis, MN (US)

( * ) Notice: Subject to any disclaimer, the term of this patent is extended or adjusted under 35 U.S.C. 154(b) by 0 days.

(21) Appl. No.: 09/315,739

(22) Filed: May 20, 1999

Related U.S. Application Data

(63) Continuation-in-part of application No. 08/880,817, filed on Jun. 24, 1997.

(51) Int. Cl.[7] .............................................. H04M 11/04
(52) U.S. Cl. .............................. 379/49; 379/38; 379/51; 455/88
(58) Field of Search .............................. 379/38, 37, 49, 379/40, 41, 51, 52; 455/88; 340/539, 531

(56) References Cited

U.S. PATENT DOCUMENTS

| | | | |
|---|---|---|---|
| 3,843,841 A | 10/1974 | Rubinstein | 179/5 P |
| 3,969,709 A | 7/1976 | Isaacs et al. | 340/224 |
| 4,237,344 A | 12/1980 | Moore | 179/2 A |
| 4,284,849 A | 8/1981 | Anderson | 179/5 R |
| 4,303,801 A | 12/1981 | Anderson | 179/5 R |
| 4,531,527 A | 7/1985 | Reinhold, Jr. | 128/696 |
| 4,712,562 A | 12/1987 | Ohayon et al. | 128/672 |
| 4,772,876 A | 9/1988 | Laud | 340/539 |
| 4,843,377 A | * 6/1989 | Fuller et al. | 379/38 |

(List continued on next page.)

OTHER PUBLICATIONS

Advertisement/Article (Mar. 1997) from Medical Care Products on an Automated Patient Phone System.

Skyroute Communications, http://www.sur-gard.com/skyroute.htm, pp. 1–4, (1974).

"21st Century Emergency Safety Communication Policy", ComCARE Alliance, http://www.comcare.org/21ct99.htm, 3 pages, (2000).

"AlarmNet–A Original Alarmnet", AlarmNet, http;//www.a-demco.com/AlarmNet/AlarmNetA.htm, pp. 1–2, (2000).

(List continued on next page.)

*Primary Examiner*—Melur Ramakrishnaiah
(74) *Attorney, Agent, or Firm*—Schwegman, Lundberg, Woessner & Kluth, P.A.

(57) ABSTRACT

A monitoring and communication system for monitoring a supervised person is provided. The system includes a preferably portable personal communication device (PCD), e.g., a portable telephone, and further includes a computer system which stores a contact plan for the supervised person and which is in two-way communication with the PCD. The computer system, using an automated phone call routine, automatically initiates the transmission of electronic voice messages or inquiries to the supervised person's PCD. The computer system records responses transmitted by the supervised person's PCD back to the computer system. The system can contact the supervised person anywhere within a service area. The supervised person responds to one or more questions or requests from the computer system by pressing appropriate keys on the PCD, thereby transmitting responses. The responses are recorded by the computer system. If the computer system does not receive a response from the supervised person's PCD or if the responses do not fall within compliance guidelines, the contact plan is forwarded to personnel for either follow up contact or to or provide other assistance. Responses, or the lack thereof, may also be forward to a third party; for example, in the case of the supervised person being a child, the third party may be a parent of the child.

39 Claims, 3 Drawing Sheets

U.S. PATENT DOCUMENTS

| | | | |
|---|---|---|---|
| 4,856,047 A | 8/1989 | Saunders | 379/57 |
| 4,908,600 A | 3/1990 | Martinez | 340/310 R |
| 4,993,059 A | 2/1991 | Smith et al. | 379/39 |
| 4,994,787 A | 2/1991 | Kratt et al. | 340/505 |
| 5,016,172 A | 5/1991 | Dessertine | 364/413.02 |
| 5,025,374 A | 6/1991 | Roizen et al. | 364/413.02 |
| 5,036,462 A | 7/1991 | Kaufman et al. | 364/413.01 |
| 5,062,147 A * | 10/1991 | Pickett et al. | 364/900 |
| 5,081,667 A | 1/1992 | Drori et al. | 379/59 |
| 5,128,979 A | 7/1992 | Reich et al. | 379/40 |
| 5,195,126 A | 3/1993 | Carrier et al. | 379/45 |
| 5,223,844 A | 6/1993 | Mansell et al. | 342/357 |
| 5,228,449 A | 7/1993 | Christ | 128/691 |
| 5,276,728 A | 1/1994 | Pagliaroli et al. | 379/58 |
| 5,278,539 A | 1/1994 | Lauterbach et al. | 340/539 |
| 5,319,355 A | 6/1994 | Russek | 340/573 |
| 5,319,698 A | 6/1994 | Glidewell et al. | 379/39 |
| 5,333,173 A | 7/1994 | Seazholtz et al. | 379/45 |
| 5,351,235 A | 9/1994 | Lahtinen | 370/58.1 |
| 5,390,238 A | 2/1995 | Kirk | 379/93 |
| 5,398,782 A | 3/1995 | Talbot et al. | 187/393 |
| 5,402,466 A | 3/1995 | Delahanty | 379/44 |
| 5,404,577 A | 4/1995 | Zuckerman et al. | 455/66 |
| 5,412,372 A | 5/1995 | Parkhurst | 340/568 |
| 5,416,695 A | 5/1995 | Stutman | 364/413.02 |
| 5,432,841 A | 7/1995 | Rimer | 379/59 |
| 5,451,839 A | 9/1995 | Rappaport et al. | 375/224 |
| 5,485,504 A * | 1/1996 | Ohnsorge | 379/58 |
| 5,486,812 A | 1/1996 | Todd | 340/539 |
| 5,513,111 A | 4/1996 | Wortham | 364/460 |
| 5,568,535 A | 10/1996 | Sheffer et al. | 379/39 |
| 5,570,083 A | 10/1996 | Johnson | 340/692 |
| 5,583,831 A | 12/1996 | Churchill et al. | 368/10 |
| 5,587,701 A | 12/1996 | Hess | 340/541 |
| 5,612,869 A | 3/1997 | Letzt et al. | 395/203 |
| 5,630,207 A | 5/1997 | Gitlin et al. | 455/54.1 |
| 5,633,910 A | 5/1997 | Cohen | 379/38 |
| 5,640,147 A | 6/1997 | Chek et al. | 340/573 |
| 5,652,564 A | 7/1997 | Winbush | 340/426 |
| 5,687,215 A | 11/1997 | Timm et al. | 379/58 |
| 5,712,619 A | 1/1998 | Simkin | 340/539 |
| 5,719,551 A | 2/1998 | Flick | 340/426 |
| 5,736,932 A | 4/1998 | Bulfer et al. | 340/825.34 |
| 5,739,748 A | 4/1998 | Flick | 340/426 |
| 5,742,233 A | 4/1998 | Hoffman et al. | 340/573 |
| 5,752,976 A | 5/1998 | Duffin et al. | 607/32 |
| 5,754,111 A | 5/1998 | Garcia | 340/573 |
| 5,777,551 A | 7/1998 | Hess | 340/541 |
| 5,784,685 A | 7/1998 | Stanford et al. | 455/31.2 |
| 5,786,746 A * | 7/1998 | Lombardo et al. | 340/286.07 |
| 5,793,283 A | 8/1998 | Davis | 340/426 |
| 5,802,014 A | 9/1998 | Danko | 368/10 |
| 5,812,536 A | 9/1998 | Manduely | 370/282 |
| 5,815,417 A | 9/1998 | Orr et al. | 364/578 |
| 5,821,854 A | 10/1998 | Dorinski et al. | 340/539 |
| 5,825,283 A | 10/1998 | Camhi | 340/426 |
| 5,832,448 A | 11/1998 | Brown | 705/2 |
| 5,845,203 A | 12/1998 | LaDue | 455/414 |
| 5,850,180 A | 12/1998 | Hess | 340/541 |
| 5,850,344 A | 12/1998 | Conkright | 364/479.01 |
| 5,852,408 A | 12/1998 | Christiansen et al. | 340/870.09 |
| H1782 H | 2/1999 | Wicks et al. | 340/825.44 |
| 5,870,020 A | 2/1999 | Harrison, Jr. | 340/426 |
| 5,873,043 A | 2/1999 | Comer | 455/458 |
| 5,874,889 A | 2/1999 | Higdon et al. | 340/426 |
| 5,892,442 A | 4/1999 | Ozery | 340/539 |
| 5,898,391 A | 4/1999 | Jefferies et al. | 340/988 |
| 5,898,904 A | 4/1999 | Wang | 455/31.3 |
| 5,902,234 A | 5/1999 | Webb | 600/300 |
| 5,907,279 A | 5/1999 | Bruins et al. | 340/506 |
| 5,917,405 A | 6/1999 | Joao | 340/426 |
| 5,933,080 A | 8/1999 | Nojima | 340/539 |
| 5,959,529 A | 9/1999 | Kail | 340/539 |
| 6,023,223 A | 2/2000 | Baxter, Jr. | 340/531 |
| 6,023,241 A | 2/2000 | Clapper | 342/357.13 |
| 6,028,514 A | 2/2000 | Lemelson et al. | 340/539 |
| 6,035,021 A * | 5/2000 | Katz | 379/93.02 |
| 6,057,758 A | 5/2000 | Dempsey et al. | 340/539 |
| 6,087,952 A | 7/2000 | Prabhakaran | 340/693.5 |
| 6,118,866 A | 9/2000 | Shtivelman | 379/309 |

OTHER PUBLICATIONS

"AlarmNet–C Control Channel Cellular", AlarmNet, http://www.ademco.com/AlarmNet/AlarmNetC.htm, 2 pages, (2000).

"AlarmNet–M Mobitex System", AlarmNet, http://www.ademco.com/AlarmNet/AlarmNetM.htm, p. 1, (2000).

"AllNetDevices:—Geoworks, Openware End Patent Fight", allNetDevices, http://www.devices.internet.com/icom$_{13}$cgi/print/print.cgi?url=http://devices.internet.com/industry/ne. . . . , 1 page, (2000).

"AllNetDevices:—The Device–Centri Home in 2000: Close, But No Cigar", allNetDevices, http://www.devices.internet.com, 3 pages, (2000).

"ARM7 Thumb Family", Arm Powered, Product Information, 4 p., (Prior to May 26, 2000).

"ARM9 Thumb Family", Arm Ltd., Product Information, 6 Pages, (Prior to May 26, 2000).

"Automatic Crash Notification", ComCARE Alliance, http://www.comcare.org/overview.htm, 2 pages, (2000).

"Blue–Connect", Acer NeWeb Corporation, Product Brief, 1 page, (Prior to May 26, 2000).

"Blue–Share", Acer NeWeb Corporation, Product Brief, 1 page, (Prior to May 26, 2000).

"Bluetooth—solutions for personal area networking", TDK Systems, Inc., Manufactures Brochure, 4 pages, (Prior to May 26, 2000).

"Bluetooth Development using SDL, MSC and TTCN", Teleogic AB, Product Information, 13 Pages, (Prior to May 26, 2000).

"Bluetooth Product Design—a natural progressionof our existing buiness", RTX, Manufactures Brochure, 4 pages, (Prior to May 26, 2000).

"Bluetooth White Paper", AU–System AB, Entire Pamphlet, (1999).

"Connect 24 Data Communications", Connect 24, http://www.connect24.com, 1 page, (2001).

"CreataLink", *Motorola, Inc.*, 2 pages, (1999).

"CreataLink 2XT", Motorola, http://www.motorola.com/MIMS/MSPG/Products/OEM/calxt, 1 page, (Mar. 1999).

"CreataLink 2XT", Motorola Messaging Products, www.mot.com/MIMS/MSPG/Products/OEM/calxt/, 1 p., (Mar. 1999).

"Designing Solutions for the Internet Economy", Intel Developer Forum Spring 2000, Program Brochure, 2 pages, (Feb. 15–17, 2000).

"Digianswer Bluetooth—Development and Demonstration Tools", Digianswer A/S, Product Sheet, 6 pages, (Prior to May 26, 2000).

"Digianswer/Bluetooth Technology", Digainswer (Irl) Ltd., Product Information, 8 Pages, (Prior to May 26, 2000).

"Emergency 911 Cellular Phone and Cellular Phone Accessories", AAA Communications, http://web.idirect.com/aaa/, 1–7 pages, (2001).

"Emergency Terms", Glossary, http://www.comcare.org/glossary.htm, 3 pages, (2000).

"Empowering the mobile enterprise", Puma Technology, Inc., Manufactures Brochure, 2 pages, (1996–1999).

"Emulation System Speeds Development of CDMA Satcom Handsets", Penton Publishing, inc., Product Information, 4 Pages, (1997).

"Enabling Innovation", Arm Ltd., Product Brochure, 10 Pages, (1999).

"Get a better vantage point and outmaneuver the competition", Cadence Design Systems, Inc., Manufactures Brochure, 2 pages, (1999).

"Introduction to the HomeRF Technical Specification", *HomeRF*, pp. 1–17, (2000).

"IVT–13 Bluetooth Protocol Stack SDL/C Source Code", Bluthtooth, Product Brochure, 2 pages, (Prior to May 26, 200).

"Lucent Technologies and Bluetooth", Lucent Technologies, Inc., Manufactures Brochure, 2 pages, (Dec. 1999).

"ObjectGEODE—The Most Advanced Integrated Environment for the Development of Distributed Real–time Systems", VERILOG S.A., Entire Brochure, (1998).

"ORA Electronics Introduces Rescue Mate, a Complete Cellular Telephone Safety Package; Hands–Free Operation, Instant Emergency 911 Access, Roadside Assistance Services", Business Wire, http://www.findarticles.com, 2 pages, (1998).

"OSE—the new generation realtime operating system", ENA OSE Systems, Informational Brochure, Entire booklet, (1999).

"PSAP Updates and Third–Party Call Centers", ComCARE Alliance, http://www.comcare.org/psap.htm, 2 pages, (2000).

"Samsung Electronics joins home radio frequency group in developement of wireless network for the home", Samsung Electronics, http://www.samsung.com/news/samsung/1998/sea0305.html, pp. 1–2, (1998).

"Socket's Bluetooth Cordless Communications Card FAQ", Socket Communications, Inc., Informational Literature, 2 pages, (Dec. 1999).

"Spontaneous Connections", CommVerge, 6 pages, (May 2000).

"Tachless Remote Engine Starters", Almex, http://www.almexltd.com/iei/mantisl200.htm, pp. 1–3, (2000).

"Technology Solutions for Bluetooth from Ericsson Microelectronics", Erricson Components AB, Manufactures Brochure, 2 pages, (Nov. 1999).

"The Ericsson Bluetooth Developement Kit—Faster launching of Bluetooth Products", Ericsson Mobile Communications, AB, Manufactures Brochure, 2 pages, (1999).

"The Secret of Success!", SIGnal Newsletter—The Official Newsletter of the Bluetooth Special Interest Group, Issue No. 3, 8 Pages, (Nov. 1999).

"UMTS W–DCMA Technology Development Using the Aptix System Explorer MP4 for Algorithm Verification", Aptix Corporation, Product Information, 4 Pages, (1999).

"Unleash the World—Core technology for Bluetooth applications", Ericsson Mobile Communications AB, Manufactures Brochure, 7 pages, (1999).

"Will the push—not pull—of Internet information dramatically alter out Web interactions", Sunworld, http://www.sunworld.com, 6 pages, (2000).

"Wireless Connections Made Easy", Bluetooth, Manufactures Brochure, 19 Pages, (Prior to May 26, 2000).

"Your Vision—Our Solution", RTX Telcom, Manufactures Brochure, 6 pages (Prior to May 26, 2000).

Houston, J., "Socket Teams with Cambridge Silicon Radio for Bluetooth Cordless Networking on Windows CE", Socket Communications, Inc., Press Release, 2 pages, (1999).

Nobel, C., "Microsoft jumps on the Bluetooth bandwagon", PC Week, 1 page, (Dec. 6, 1999).

Posti, J., "Motorola Introduces CreataLink 2 XT ReFLEX Two–way Data Transceiver for Wireless Communications", Motorola Press Release, www.mot.com/MIMS/MSPG/Press/PRI9990303$_{13}$21575.html, 2 p., (Mar. 1999).

\* cited by examiner

MONITORING AND COMMUNICATION SYSTEM FOR STATIONARY AND MOBILE PERSONS

This document is a continuation-in-part of U.S. Patent Application Ser. No. 08/880,817, filed on Jun. 24, 1997, which is a continuation-in-part of co-owned U.S. Patent Application Ser. No. 08/837,229, filed on Apr. 10, 1997 and issued on May 11, 1999 as U.S. Pat. No. 5,902,234, both of which are hereby incorporated by reference herein in their entirety.

BACKGROUND OF THE INVENTION

1. Field of the Invention

This invention relates broadly to monitoring and communication systems. More particularly, this invention relates to monitoring and communication systems for stationary mobile persons.

2. State of the Art

The workforce of today is primarily composed of individuals who lead busy non-traditional lifestyles. In most two parent households, both the father and mother work. In single parent households, the sole parent invariably has to work in addition to nurturing the children. The traditional model of the father going to work while the mother remains at home to care for the children is either a luxury few families can afford, or a choice many parents no longer select.

Many working parents are also discovering that their work environment is changing, becoming more mobile and unpredictable. Salespersons need to be constantly on the road and managers find themselves caught up in unexpected meetings. Many employees are directed to perform multiple jobs often in different locations day to day. As a result, many working adults do not know where they will be at any given time.

This busy and mobile lifestyle is often in conflict with the responsibilities normally associated with being at home, or at least available, for children. Children need to be reminded to take medications, prodded to get dinner started or to feed the family pet, and desire to be contacted about their well-being. In addition, parents want to know about the well-being and security of their children. However, a phone call by a working parent to his or her child to inquire about the safety, activities, and general happiness of the child is often difficult. Most working adults find the task of balancing schedules, calling someone on a daily basis, or just being available every day at the same time and place (to receive phone calls) to be very difficult. While a babysitter is one solution to the situation, a good babysitter can be difficult to find and also quite costly. Moreover, some children may feel that they are too mature to have a babysitter, yet the children may still require some level of supervision. There is a need for a means for supervising children which is cost-effective and which will provide the parent with assurance of the well-being of the child. In addition, such supervision must meet the needs of a mobile child.

Likewise, members of the senior citizen community that live at home can often use, or at least often desire, their children's or friends' attentiveness; i.e., a phone call confirming all is well. But for the same reasons, such phone calls can be difficult to make at times when they are needed most by the senior citizens. Moreover, some senior citizens, while not in need of costly care by a human care provider or costly monitoring by state-of-the-art telemedicine devices, are nevertheless in need of assistance to remember to take critical medications and attend appointments.

SUMMARY OF THE INVENTION

It is therefore an object of the invention to provide a monitoring and communication system which can automatically contact a supervised person to ensure their well-being and to provide the supervised person with necessary reminders.

It is another object of the invention to provide a monitoring and communication system which ensures compliance with certain predetermined responsibilities by the supervised person.

It is a further object of the invention to provide a monitoring and communication system which can monitor and communicate with a supervised person at or away from home.

It is an additional object of the invention to provide a monitoring and communication system which provides interactivity and a degree of multilevel inquiry.

It is also an object of the invention to provide a monitoring and communication system which can, based upon responses by the supervised person, if necessary, contact a third party.

In accord with these objects which will be discussed in detail below, a monitoring and communication system for monitoring a child, a senior citizen, an ambulatory home-care patient, or another person requiring supervision (hereinafter 'supervised person') is provided. The system includes a personal communication device ('PCD') carried or worn by the supervised person (e.g., a portable telephone or pager) or at the home of the supervised person (e.g., a home-based telephone) and further includes a computer system which stores a contact plan for the supervised person and which is in two-way communication with the PCD. The computer system, using an automated phone call routine, automatically initiates the transmission of electronic voice messages or inquiries to the supervised person's PCD. The computer system records responses transmitted by the supervised person's PCD back to the computer system. The system can contact the supervised person at home or anywhere within a service area, and preferably anywhere serviced by the system on which the PCD operates. The supervised person responds to one or more questions or requests from the computer system by pressing appropriate keys on the PCD or by providing voice responses, thereby transmitting responses. The responses are recorded by the computer system. If the computer system does not receive a response from the supervised person's PCD or if the responses do not fall within compliance guidelines, the contact plan is forwarded to a staff member for either follow up contact or to provide other assistance. Responses, or the lack thereof, may additionally or alternatively be forwarded to a guardian or third party; for example, in the case of the supervised person being a child, the third party may be a parent of the child.

It will be appreciated that the monitoring and communication system of the invention permits a supervised person to be contacted within and outside the home of the supervised person, as the PCD may be home-based or portable. Therefore, the supervised person is not confined to his/her home in order to respond to a monitoring system stationed in his/her home. In addition, a multi-level inquiry may be established to determine the condition of the supervised person and the details of the inquiry and the responses are stored in the computer system to verify and evidence that an appropriate response by the supervised person to the computer system has been provided. Moreover, the monitoring and communication system is relatively inexpensive, especially when compared with human care givers (e.g., babysitters or nurses) and complex telemedicine systems. Furthermore, the interactivity, and level of inquiry, between the supervised person and the computer system is reassuring to the supervised person.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
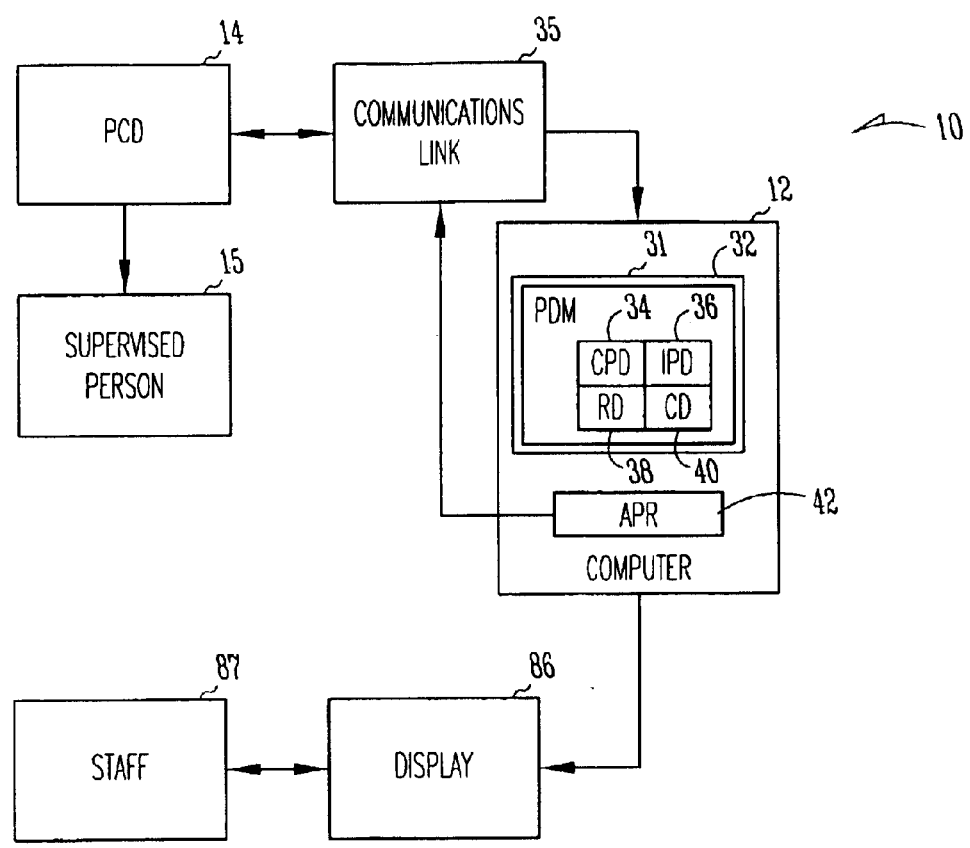
FIG. 1 is a schematic of the monitoring and communication system according to the invention.

Turning now to FIG. 1, an overview of a monitoring and communication system 10 is shown. Generally, the system 10 includes a computer system 12 housed at a monitoring and communication provider facility and a two-way personal communication device (PCD) 14 operable by a supervised person 15. 'Supervised person' as used herein refers to a child, a senior citizen, an ambulatory home-care patient, or other person to be monitored by and in communication with the monitoring and communication system of the invention. 'Subscriber' as used herein refers to the person subscribing to the service provided by the monitoring and communication system described herein, and is most likely to be a guardian of the supervised person, but may also be the supervised person. As described in more detail below, the computer system 12 is arranged to be in two-way communication with the PCD 14.

Figure 2:
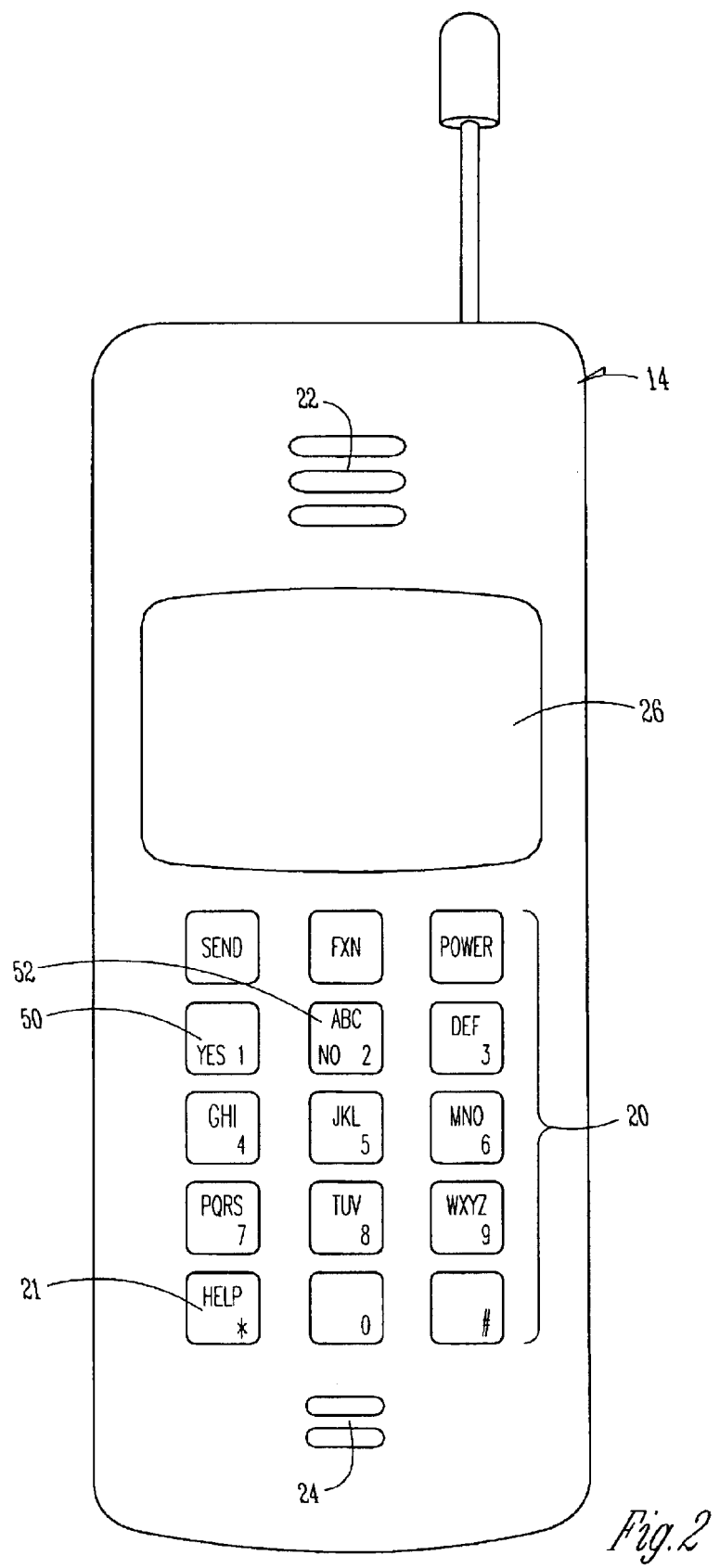
FIG. 2 is a front view of a perspective view of a personal communication device for the monitoring and communication system of the invention.

Referring to FIG. 2, the PCD 14 is preferably a portable communication device (e.g., a cellular telephone) having a digital to multiple frequency (DTMF) keypad 20 having keys and a speaker 22. The PCD preferably also includes a microphone 24 and an alphanumeric display 26. One of the keys 21 is optionally programmed for quickly calling emergency assistance. Another preferred PCD is a two-way paging device having alphanumeric display, as described in detail in previously incorporated co-owned Ser. No. 08/837,229. A stationary PCD, e.g., a home-based telephone, may also be used.

Turning back to FIG. 1, the computer system 12 includes a memory or memories 31 which includes a personal data module (PDM) 32, preferably being stored as a software data array. The PDM 32 includes information about a plurality of supervised persons. For example, for each supervised person, PDM information may include the supervised person's name, PCD number (e.g., mobile phone number), personal password (described below), voice identification characteristics, contact plan data (CPD) 34, inquiry plan data (IPD) 36, response data (RD) 38, compliance data (CD) 40, home phone number, home address, medical condition, age, health care provider, third party contact phone numbers (e.g., relatives and neighbors), emergency medical services local to the home of the supervised person, and any or all other pertinent data related to the supervised person. The contact plan data (CPD) 34 includes indications of a schedule for automatically contacting the supervised person. The inquiry plan data (IPD) 36 includes indications of inquiries regarding the condition of the supervised person, indications of inquiries regarding actions that should be performed by the supervised person, e.g., pharmacological administration (what medicines to self-administer and when), indications of inquiries regarding where the supervised person should be located at a particular time, e.g., at home after-school, and indications of any other inquiries that are desired to be made. The indications of inquiries of the IPD 36 are preferably sent to the PCD in a form which is easily understood by the supervised person, e.g., electronic voice message and/or text-based messages. The compliance data (CD) 40 includes indications of acceptable responses input by the supervised person in response to receiving, on the PCD, inquiries. In a preferred embodiment of the invention, the indications of inquiries of the IPD 36 are stored voice recordings which were recorded by a person into memory 31. As such, it will be appreciated that the stored voice recordings may be made by a person (e.g., a parent) concerned about the supervised person, and who most likely is 'the subscriber' to the service provided by the monitoring and communication system. Thus, the supervised person may receive the inquiries in a voice familiar and comforting to them. Moreover, the voice recordings may be changed at any time by 'the subscriber' by calling an operator working with the computer system 12, or directly calling the computer system, entering account information and preferably a password, and then adding or deleting messages, as desired.

According to the contact plan data (CPD) 34 in the PDM 32, inquiry plan data (IPD) 36 is sent at prescribed days and times to a communications link 35 (e.g., an antenna 35) and transmitted (e.g., via cellular transmission systems such as an 850 MHz cellular systems or micro-cellular systems such as PCS digital wireless systems), to the PCD 14 provided to the supervised person 15. For example, a series of inquiries may be sent in a script form to a child such as the following series of questions and requests, available responses, and comments:

Did you take your 3:00 pm asthma medication?
        (Press 1 for 'Yes', press 2 for 'No')
    Did you walk the dog?
        (Press 1 for 'Yes', press 2 for 'No')
    Did you do your homework?
        (Press 1 for 'Yes', press 2 for 'No')
    Will you be home at dinner time?
        (Press 1 for 'Yes', press 2 for 'No')
    Do you need to speak with an operator?
        (Press 1 for 'Yes', press 2 for 'No')

In addition, a more suitable script may be sent to a senior citizen:

Did you take your 12 pm heart medication?
        (Press 1 for 'Yes', press 2 for 'No')
    Did you experience any unusual side effects?
        (Press 1 for 'Yes', press 2 for 'No')
    Would you like to speak with an operator?
        (Press 1 for 'Yes', press 2 for 'No')
    Would you like a follow-up contact in two hours?
        (Press 1 for 'Yes', press 2 for 'No')

While responses to the inquiries can be input as DTMF responses from the keypad of the PCD, as indicated, it is preferable that when the PCD has a microphone, responses be made via spoken word, as described further below.

In addition, to prevent tampering with the operation of the monitoring system, the PDM 32 preferably includes security features. One of two preferable security measures may be used. First, the PDM 32 may include a password feature in which the PDM stores a personal password (or numerical identification number) for a supervised person. The personal password (or identification number) must be keyed into the PCD 14 and confirmed by comparison with a personal password stored for that supervised person in the PDM 32 of the computer system 12. An alternate or additional security feature, using existing technology, matches voice identification characteristics (i.e., a voice print) of the person providing responses with a voice identification characteristics stored in the PDM 32 to verify that the person providing responses is the supervised person. It will be appreciated that such a feature is especially desirable in the supervision of a child who may ask another child (sibling or friend) to provide responses in their place.

The response data (RD) 38 is a record of detailed information regarding communications between the supervised person 15 and the computer system 12 and may be implemented as an analog (e.g. tape) recorder or a digital (e.g. disk memory) recorder. The detailed information may include, for example, the time and date of all attempted communications, the supervised person's responses to a script of inquiries in the communications, and contacts of additional persons, as per the contact plan. The RD 38 is compared to compliance data 40 to confirm that the supervised person 14 is satisfactorily responding to the IPD 36 inquiries. The RD 38 also serves as a quality assurance record. In addition, the computer system 12 uses information stored as RD 38 to provide reporting functions (e.g., charges for the service of monitoring and communication, statistical analysis, and charting) regarding the communications between the supervised person and the computer system. For example, the computer system 12 may provide a "dropout ratio" for a supervised person; i.e., the predictability of receiving a response from that particular person. The "dropout ratio" is a measure of the effectiveness of the technology for a particular supervised person and may be used to determine when a particular supervised person needs to be removed from the technology of the invention and supervised through more conventional means. The reporting functions may also be used to adjust the time period for the "timeout", defined and described hereinafter. It will be appreciated that reporting functions (e.g., printed reports) may be provided to a third party or directly to the supervised person, especially when the supervised person is 'the subscriber'.

Figure 3:
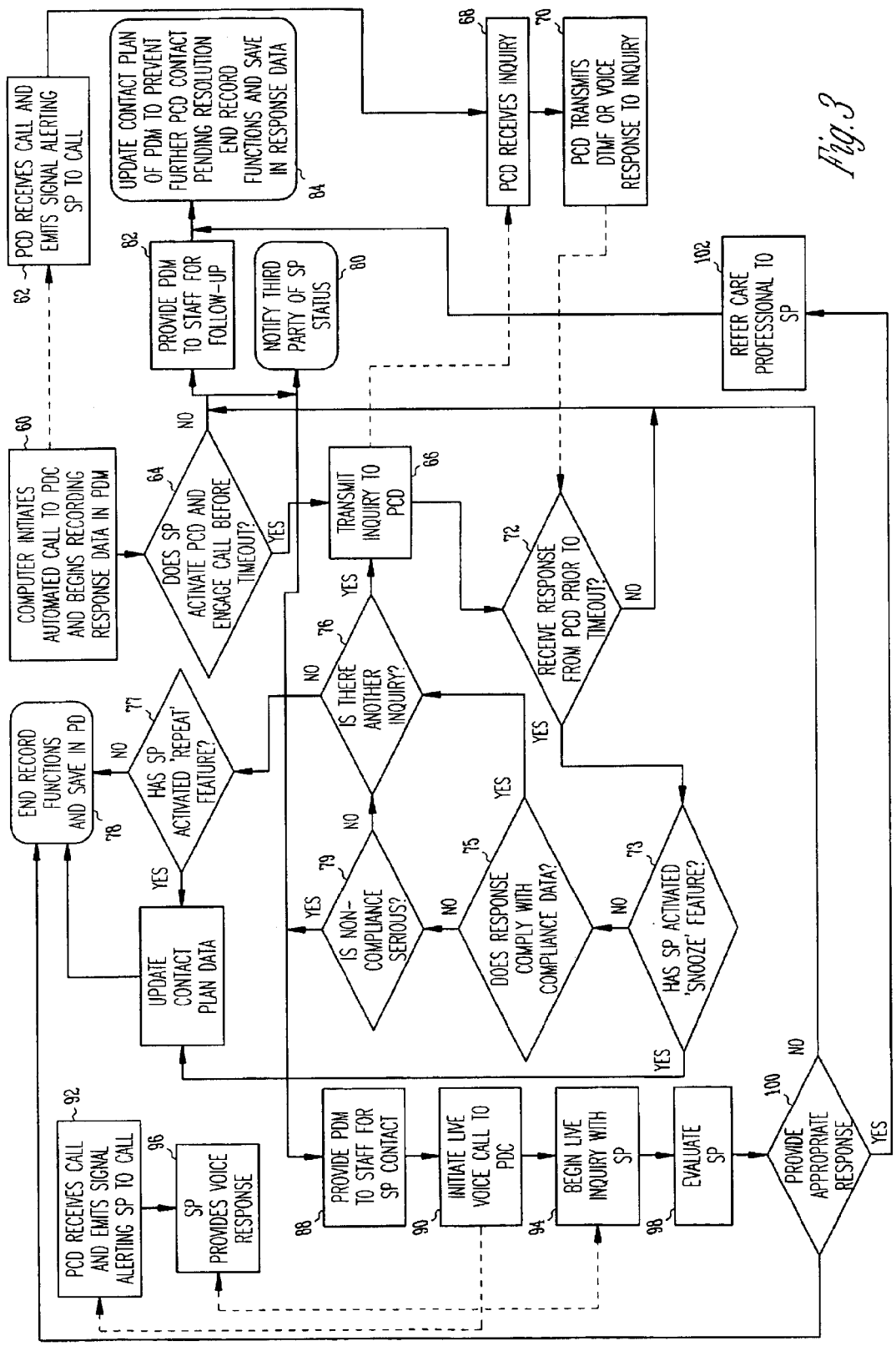
FIG. 3 is a flow diagram of the operation of the monitoring and communication system, with communication between the computer system and a person indicated by dashed lines.

The computer system 12 determines which supervised persons are to be contacted, and when they are to be contacted, based upon contact plans stored in the PDM 32 and a clock (not shown) of the computer system. Referring to FIGS. 1, 2 and 3, when a supervised person is to be contacted, the computer system 12, at 60, starts recording the RD 38 and initiates an automated communication using an automated phone call routine (APR) 42. The APR 42 is preferably provided as software in the computer system 12 and transmits, typically via antenna 35, a call to a supervised person's PCD 14, preferably using commercially available telecommunication hardware and/or software and/or PCD contact software implemented elsewhere on the computer system.

With reference to FIG. 3, at 60, the APR 42 of the computer system initiates a call to the supervised person's PCD. When, at 62, the PCD receives a call, a signal is emitted by the PCD to alert the supervised person (denoted 'SP' in FIG. 3) to the call. Preferably, the speaker 22 of the PCD sounds a series of tones to alert the supervised person of the incoming call. At 64, the computer system determines whether the supervised person has activated the PCD within a given time frame ("timeout"). If not, the computer system will proceed at 80 and 82, as described hereinafter. If the supervised person does respond before the timeout, the timeout is reset and, at 66, a first voice message inquiry (e.g., "Please enter your password" presumably being a desired first inquiry) is transmitted by the computer system 12 to the PCD 14. The PCD, at 68, receives the first voice message inquiry and provides the inquiry to the supervised person 15, preferably audibly via through the speaker 22, and preferably additionally as a text-based message displayed on the alphanumeric display 26.

A variety of inquiries and response types are possible: 'Yes' and 'No' answerable questions, inquiries requiring alphanumeric responses, and inquiries requiring other spoken word or keyed responses. The supervised person is preferably cued to respond to 'Yes' and 'No' answerable questions by pressing keys on the DTMF keypad 20 of the PCD 14 which correspond to a 'Yes' or 'No' response. Keys (e.g., keys 50, 52, in FIG. 2) are preferably provided with 'Yes' and 'No' indicia to assist the supervised person in keying in a desired response, where applicable. In all questions in which a response is preferably keyed in, it will be appreciated that in the alternative, or in addition, responses may be spoken into the PCD microphone 24 and "translated" using voice recognition software stored at the computer system. For example, in response to the inquiry being a password request, the supervised person may either key in the password on the DTMF keypad of the PCD or speak the password or alphanumeric characters of the password into the PCD microphone.

If the supervised person does not respond to the question within an appropriate period of time (prior to timeout), the computer system will proceed at 80, 82 and 84 as described hereafter. However, if the supervised person does respond within the timeout, the responses are transmitted, at 70, by the PCD and received, at 72, by the computer system 12.

According to a preferred aspect of the invention, the system is preferably provided with a 'snooze' feature which can be operated by the supervised person with a dedicated key on the PCD, via a spoken word, or via a key combination, at any time during the inquiry and response (i.e., a supervised person can request that the monitoring and communication system delay the current inquiry until a later time, e.g., in an hour). If the 'snooze' is activated at 73, the contact plan data 34 is updated at 74 so that the computer will reinitiate contact at a later time.

If the 'snooze' feature is not activated at 73, the response is compared with the compliance data (CD) 40 and if the response matches or is within limits of the CD, at 75, the computer system then sends the next inquiry (if there is another inquiry), at 76, to the supervised person, as described above, and the process is repeated until there are no further inquiries in the inquiry plan data (IPD) 36. Alternatively all inquiries of the IPD 36 may be sent to the PCD and all responses received prior to comparing the responses in the response data (RD) 38 to the CD 40. In either case, if the RD 38 is in agreement with the CD 40, then at 78, the present inquiry is ended by terminating recording functions and storing at 78 all responses. According to another preferred aspect of the invention, a 'repeat' feature is provided and selectable by the supervised person such that the supervised person can elect to repeat the contact and inquiry at a later time (e.g., in an hour). If the repeat function is activated at 77, prior to ending the inquiry, the contact plan data (CPD) 34 is updated at 88. In addition, the contact plan may be programmed to contact and provide the subscriber or a third party with information regarding the agreement between the RD 38 and the CD 40.

If the supervised person fails at 64 to operate the PCD (i.e., answer the call) or respond to the PCD inquiry within a given time frame ("timeout") (for example, one minute), the computer system, at 80, may contact a third party (e.g., a parent) and deliver a recorded message of the failure to contact the supervised person or alternately a live operator may contact the third party. In addition, at 82 the computer 12 also preferably displays the PDM data on a display 86 (FIG. 1) monitored by an operator or other staff member 87 and updates at 84 the CPD 34 of the PDM 32 to prevent further scheduled PCD contact pending a satisfactory resolution regarding the supervised person's whereabouts and condition. Additionally, the attempt to contact the supervised person 15 via PCD is recorded and stored at 84. The staff member reviews the supervised person's data, including telephone numbers for relatives, neighbors, and emergency medical services personnel local to the home of the supervised person, and instructions stored in the PDM for a recommended cause of action based on failure to contact the supervised person. For example, the recommended course of action for a particular supervised person may instruct the staff member to send emergency medical services personnel to the home of the supervised person to investigate; for another supervised person the recommended action may be an attempt to contact a guardian of the supervised person; while for another supervised person, emergency action may only be taken if the failure to contact the supervised person continues over a period of time. The prescribed action is entered as part of the supervised person's PDM data and record functions are ended and stored in the RD 38.

If the supervised person answered the PCD, but provided answers which were determined at 75 to be non-complying, depending on the 'degree' (or seriousness) of non-compliance at 79, the computer system 12 preferably either takes no remedial action or notifies, at 80, a third party (e.g., a parent or guardian) and/or displays at 89 the PDM 32 for the supervised person 15 on the display screen 86 monitored by the staff member 87 for further review. For example, a non-serious non-compliant answer would be a 'No' response in response to an inquiry to a child regarding whether the child has started his or her homework. On the other hand, a 'No' response with respect to whether critical medication has been taken, may require further review. As such, the appropriate action for a non-compliant response at 79 to a particular inquiry may be programmed into the PDM 32. In either case, a record of non-serious non-compliant answers are stored for review by a guardian of the supervised person. While not described in FIG. 3 (in order that the complexity of FIG. 3 not detract from its utility), it will be appreciated that a non-compliant response to a password inquiry preferably causes notification of a third party at 80 and ends the inquiry session at 78, but does not initiate contact from staff.

If the non-compliant response requires further review at 89, the staff member preferably reviews the supervised person's PDM data to briefly assess the exigency of the circumstance and may, if appropriate, initiate at 90 a live call to the supervised person's PCD to speak with the supervised person. The PCD 14, at 92, receives the call and emits a signal alerting the supervised person 15 to the call. Once contact with the supervised person is established at 93, the staff member 84 and the supervised person 15 engage in an inquiry and response, at 94 and 96, respectively, such that the staff member is able to evaluate, at 98, the condition of the supervised person. The staff member provides an appropriate response at 100, either by concluding that the supervised person's condition is presently satisfactory and ending the inquiry session, at 78, by contacting a guardian of the supervised person as indicated at 80, by referring other staff to the supervised person as indicated at 82, by referring other care professionals (e.g., police or emergency medical personnel) to the home of the supervised person as indicated at 102, or by any other appropriate response. The conversation and staff member's recommended response are stored (at 78 or 84) in the RD. If personal intervention is required at 80, 82, or 102, the PDM for the supervised person is also adjusted at 84 to prevent further automated calls to the supervised person's PCD pending resolution of the matter so that the same situation will not be repeated hours later unnecessarily. If contact was unable to be established at 93, the staff provides an appropriate response at 100 depending on the nature of the inquiry and non-complying response which triggered the attempted contact of the supervised person.

It will be appreciated that the monitoring and communication system permits a person for whom it is desirable to be under some level of supervision to be contacted within and outside the home of that person, as the system for interacting with the person is preferably a portable two-way PCD which operates over a relatively large area. Therefore, the supervised person is not confined to his/her home in order to respond. In addition, a multi-level inquiry is established to determine the well-being of the supervised person and the questions of the inquiry and the responses are stored in the computer system to verify and evidence that an appropriate response by staff member to the responses supplied by the supervised person has been provided. Moreover, the PCD is relatively inexpensive, especially when compared with current telemedicine systems or personnel care by a babysitter or visiting nurse, and provides a level of interactivity which is reassuring to the supervised person.

There have been described and illustrated herein a monitoring and communication system and a method of communicating with stationary and mobile supervised persons to ensure the person's well-being. While particular embodiments of the invention have been described, it is not intended that the invention be limited thereto, as it is intended that the invention be as broad in scope as the art will allow and that the specification be read likewise. It will be appreciated that other portable communication devices may also be used to provide two-way voice or text messaging. For example, the ENVOY by Motorola, Inc., (a hand-held portable computer system with a modem), other portable computers with modems, personal digital assistants (PDAs), or a commercial two-way radio having 800–900 MHz trunking with DTMF capability are all appropriate. In fact, any communication device meeting the needs of the described system can likewise be used. Likewise, while cellular transmission has been disclosed, other transmission system can be used; e.g., radio transmission system. Moreover, the computer system can be set up to contact the supervised person first at a stationary phone and, if no answer, next at a portable phone, and if no answer, next at another portable communication device, e.g., a pager, etc. Furthermore, the computer system may attempt contacts at different stationary phones. Also while the PCD has been disclosed to include a sound emitter, it will be appreciated that the PCD may be designed to emit light and/or vibration for the hearing impaired. In addition, while the PCD has been shown to preferably include a 'help' button to automatically dial an emergency phone number, it will be appreciated that the PCD may include other buttons programmed for particular functions. Also, while the PCD is described as preferably having an alphanumeric display, it may, in the alternative or in addition, have an iconic display. In addition, the PDM may include information other than that particularly described above; for example, exercise schedules, general perceived state of health, doctor appointments, and more may all be provided. Likewise, the inquiry scripts may include reminders of scheduled appointments, directives or compliance questions regarding dietary restrictions, directives or compliance questions regarding exercise regimens, and whether the supervised person will be available to answer the next scheduled inquiry (i.e., certain supervised persons can be given the option to defer a later scheduled contact). Also while certain features, e.g., 'snooze' and 'repeat', have been described, it will be appreciated that not all features need be made available to a supervised person or even provided in the computer system. Likewise the features of the invention may be otherwise altered or implemented in a system which varies from the flow diagram of FIG. 3. In addition, while it is preferable to pass the PDM data of a supervised person supplying non-complying answers to a staff member for review, it will be appreciated that the computer system can be configured to automatically place a call directing emergency staff to the home of the supervised person without prior staff review, or to automatically call a guardian, or other third party with an indication that the supervised person is providing non-complying responses. Also, responses of the supervised person may be checked for compliance after all inquiries have been sent and after all responses have been received, or as each response is received by the computer, such that a non-complying response can immediately trigger staff personnel to initiate a follow-up procedure. In addition, while the PDM has been described as having data stored distinctly as IPD, CPD, RD, and CD, it will be appreciated that the PDM may store data otherwise. Moreover, while the computer system has been described as being at located at a provider facility, it will be appreciated that portions of the computer system may be provided at different locations. It will therefore be appreciated by those skilled in the art that yet other modifications could be made to the provided invention without deviating from its spirit and scope as so claimed.

We claim:

1. A monitoring and communication system for a supervised person, comprising:

a) a computer system having a memory means, an automated calling means, a first receiving means, and a verifying means, said memory means for storing indications of personal data of the supervised person including indications of a contact schedule and inquiry data; and b) a communication means for communication between the supervised person and the computer system and having a second receiving means, at least one of an audio means and a visual means coupled to said 2nd receiving means, an input means, and a transmitting means coupled to said input means, said automated calling means for automatically calling said communication means according to said contact schedule and transmitting said inquiry data from said computer system to said communication means, said verifying means for verifying that a responder utilizing said communication means is the supervised person, said second receiving means for receiving said inquiry data and providing said inquiry data to said at least one of an audio means and a visual means for presentation to the supervised person, said input means for permitting the person to provide a response to said inquiry data for transmission by said transmitting means, and said first receiving means for receiving at said computer system said response transmitted by said transmitting means.

2. The monitoring and communication system according to claim 1, wherein:

said indications of personal data further includes indications of compliance and said computer system includes means for comparing said response with said indications of compliance to determine whether the response is within the bounds of said indications of compliance.

3. The monitoring and communication system according to claim 1, wherein:

said inquiry data is at least one voice message.

4. The monitoring and communication system according to claim 3, wherein:

said computer system further includes a recording means for recording a response to said at least one voice message.

5. The monitoring and communication system according to claim 1, wherein:

said input means is at least one of an alpha input means, a numeric input means, and an audio input means.

6. The monitoring and communication system according to claim 1, wherein:

said input means is a digital to multiple frequency keypad.

7. The monitoring and communication system according to claim 1, wherein:

said at least one of an audio means and a visual means comprises an alphanumeric display.

8. The monitoring and communication system according to claim 1, wherein:

said verifying means comprises indications of at least one of a password, a numerical identification number, and voice identifying characteristics stored in said personal data.

9. The monitoring and communication system according to claim 1, wherein:

said computer system further includes a recording means for recording said first response.

10. The monitoring and communication system according to claim 1, wherein:

said computer system further includes a reporting means for reporting communications with the supervised person.

11. The monitoring and communication system according to claim 1, further comprising:

c) timeout means for causing said computer system to contact a third party when said first receiving means fails to contact said communication means or to receive said response from said communication means within a predetermined period of time after said automated calling means automatically calls said communication means.

12. A monitoring and communication system for use by a mobile supervised person, comprising:

a) a computer system having a memory means, an automated calling means, and a first receiving means, said memory means for storing indications of a personal data module for the supervised person including indications of a contact schedule and inquiry data; and b) a portable communication device adapted to be carried by the supervised person and having a second receiving means, at least one of an audio means and a visual means coupled to said receiving means, an input means, and a transmitting means coupled to said input means, said automated calling means for automatically calling said portable communication device according to said contact schedule and transmitting said inquiry data from said computer system to said portable communication device, said second receiving means for receiving said inquiry data and providing said inquiry data to said at least one audio means and visual means for presentation to the supervised person, said input means for permitting the supervised person to provide a response to said inquiry data for transmission by said transmitting means, and said first receiving means for receiving at said computer system said response transmitted by said transmitting means.

13. The monitoring and communication system according to claim 12, wherein:

said indications of personal data further includes indications of compliance and said computer system includes means for comparing said response with said indications of compliance to determine whether the response is within the bounds of said indications of compliance.

14. The monitoring and communication system according to claim 12, wherein:

said inquiry data is at least one voice message.

15. The monitoring and communication system according to claim 12, wherein:

said computer system further includes a recording means for recording a response to said at least one voice message.

16. The monitoring and communication system according to claim 12, wherein:

said input means is at least one of an alpha input means, a numeric input means, and an audio input means.

17. The monitoring and communication system according to claim 12, wherein:

said input means is a digital to multiple frequency keypad.

18. The monitoring and communication system according to claim 12, wherein:

said at least one of an audio means and a visual means comprises an alphanumeric display.

19. The monitoring and communication system according to claim 12, wherein:

said portable communication device is one of a cellular telephone and a pager.

20. The monitoring and communication system according to claim 12, wherein:

verifying means for verifying that a responder using said communication device is the supervised person.

21. The monitoring and communication system according to claim 20, wherein:

said verifying means comprises indications of one of a password, a numerical identification number, and voice identifying characteristics stored in said personal data.

22. The monitoring and communication system according to claim 12, wherein:

said computer system further includes a recording means for recording said first response.

23. The monitoring and communication system according to claim 12, wherein:

said computer system further includes a reporting means for reporting communications with the supervised person.

24. The monitoring and communication system according to claim 12, further comprising:

c) timeout means for causing said computer system to contact a third party when said first receiving means fails to contact said communication device or to receive said response from said communication device within a predetermined period of time after said automated calling means automatically calls said communication device.

25. A method of communicating with a supervised person to provide a degree of supervision to the supervised person, comprising:

a) providing a portable communication device to the supervised person;

b) initiating a contact by a computer to the portable communication device at a first time determined by a contact plan stored at the computer and at a second time selected by the supervised person;

c) automatically transmitting an inquiry message from the computer system to the portable communication device; and d) in response to the supervised person inputting into the portable communication device a response to the inquiry message, receiving at the computer system the response from the portable communication device.

26. A method according to claim 25, wherein:

the response is a voice message.

27. A method according to claim 25, further comprising:

e) comparing the response to indications of compliance stored in the computer system; and f) determining whether the response is in agreement with the indications of compliance.

28. A method according to claim 27, further comprising:

g) making human contact with the supervised person; and h) based on said making human contact, performing an action.

29. A method according to claim 27, further comprising:

g) if the response is not in agreement with the indications of compliance, contacting another person.

30. A method of according to claim 25, wherein:

the inquiry message is transmitted from the computer system to the portable communication device via one of a cellular system and a radio-based system.

31. A method according to claim 25, further comprising:

e) recording the response in a memory means for storing responses.

32. A method according to claim 25, further comprising:

e) reporting the contact to at least one of the person and a second person.

33. A method according to claim 25, further comprising:

e) statistically analyzing the frequency of successfully receiving at the computer system a response relative to contact attempts by the computer system to the portable communication device.

34. A method according to claim 25, further comprising:

e) verifying that a responder using the communication device is the supervised person.

35. A method according to claim 34, wherein:

said verifying includes comparing at least one of a password, a numerical identification number, and a voice identifying characteristic input by the responder with the same of at least one of a password, a numerical identification number, and a voice identifying characteristic of the supervised person stored in the computer system.

36. A method according to claim 25, wherein:

said inquiry message is a voice message.

37. A method according to claim 36, further comprising:

e) at least one of adding and deleting inquiry messages, wherein said inquiry message was recorded by a supervisor of the supervised person, and at least one of adding and deleting inquiry messages comprises the supervisor contacting the computer system and providing to the computer system a password.

38. A method according to claim 25 wherein initiating the contact at the second time includes receiving an input from the supervised person to delay the contact by a snooze delay time.

39. A method according to claim 25 wherein initiating the contact at the second time includes receiving an input from the supervised person to repeat the contact at a later time.

* * * * *